(12) United States Patent
Figg et al.

(10) Patent No.: US 8,716,315 B2
(45) Date of Patent: May 6, 2014

(54) ANALOGS OF THALIDOMIDE AS POTENTIAL ANGIOGENESIS INHIBITORS

(75) Inventors: William D. Figg, Fairfax, VA (US); Kurt Eger, Leipzig (DE); Uwe Teubert, Hameln (DE); Michael Weiss, Bethesda, MD (US); Michael Guetschow, Bonn (DE); Thomas Hecker, Erfurt (DE); Sunna Hauschildt, Leipzig (DE)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 1410 days.

(21) Appl. No.: 11/880,404

(22) Filed: Jul. 19, 2007

(65) Prior Publication Data

US 2007/0293519 A1 Dec. 20, 2007

Related U.S. Application Data

(63) Continuation of application No. 10/469,359, filed as application No. PCT/US02/05868 on Feb. 26, 2002, now Pat. No. 7,320,991.

(60) Provisional application No. 60/271,941, filed on Feb. 27, 2001.

(51) Int. Cl.
*A61K 31/445* (2006.01)

(52) U.S. Cl.
USPC ......................................................... 514/323

(58) Field of Classification Search
USPC .......................................................... 514/323
See application file for complete search history.

(56) References Cited

U.S. PATENT DOCUMENTS

| 2,830,991 | A | 4/1958 | Keller et al. |
| 3,314,953 | A | 4/1967 | Vazakas et al. |
| 3,320,270 | A | 5/1967 | Grogan et al. |
| 3,560,495 | A | 2/1971 | Frankus et al. |
| 3,794,641 | A | 2/1974 | Görög et al. |
| 4,092,147 | A | 5/1978 | Ashkar |
| 4,291,048 | A | 9/1981 | Gold et al. |
| 5,434,170 | A | 7/1995 | Andrulis, Jr. |
| 5,593,990 | A | 1/1997 | D'Amato |
| 5,605,684 | A | 2/1997 | Piacquadio |
| 5,629,327 | A | 5/1997 | D'Amato |
| 5,712,291 | A | 1/1998 | D'Amato |
| 5,783,605 | A | 7/1998 | Kuo et al. |
| 5,789,434 | A | 8/1998 | Kluender et al. |
| 5,840,724 | A | 11/1998 | Fenton et al. |
| 6,071,948 | A | 6/2000 | D'Amato |
| 6,080,742 | A | 6/2000 | Germann et al. |
| 6,096,768 | A | 8/2000 | Ashton et al. |
| 6,110,941 | A | 8/2000 | Zimmer et al. |
| 6,124,322 | A | 9/2000 | Bjoerkman et al. |
| 6,235,756 | B1 | 5/2001 | D'Amato |
| 6,306,879 | B1 | 10/2001 | Germann et al. |
| 6,417,197 | B1 | 7/2002 | Schneider et al. |
| 6,420,414 | B1 | 7/2002 | D'Amato |
| 6,429,212 | B1 | 8/2002 | Hashimoto |
| 6,458,810 | B1 | 10/2002 | Muller et al. |
| 6,469,045 | B1 | 10/2002 | D'Amato |
| 6,500,845 | B1 | 12/2002 | Boehlke et al. |
| 6,518,298 | B2 | 2/2003 | Green et al. |
| 6,555,554 | B2 | 4/2003 | Muller et al. |
| 6,762,195 | B2 | 7/2004 | Muller et al. |
| 2001/0041716 | A1 | 11/2001 | Laing et al. |
| 2002/0022627 | A1 | 2/2002 | Dannenberg |
| 2002/0161023 | A1 | 10/2002 | D'Amato |
| 2003/0013739 | A1 | 1/2003 | Masferrer |
| 2003/0181428 | A1 | 9/2003 | Green et al. |
| 2005/0004087 | A1 | 1/2005 | D'Amato et al. |

FOREIGN PATENT DOCUMENTS

| CA | 2104776 | 8/1992 |
| CA | 2251060 | 3/1997 |
| CA | 2228385 | 1/1998 |
| CA | 2248838 | 10/1998 |
| CA | 2302886 | 3/2000 |
| DE | 33 32 633 A1 | 4/1985 |
| EP | 0 688 771 A1 | 12/1995 |
| EP | 0 856 513 A2 | 8/1996 |
| EP | 0 908 176 A1 | 4/1999 |
| EP | 0 688 771 A2 | 7/2001 |
| EP | 1 336 602 A1 | 8/2003 |
| GB | 962857 | 7/1964 |
| GB | 1075420 | 7/1967 |
| GB | 1049283 | 11/1996 |
| JP | 10-109975 | 4/1998 |
| WO | WO 92/18496 | 10/1992 |
| WO | WO 94/20085 | 9/1994 |
| WO | WO 95/17154 | 6/1995 |

(Continued)

OTHER PUBLICATIONS

Niwayama et al. "Enhanced potency . . . " Bioorganic & Med.Chemi Lett. v.8 p. 1071-1076 (1998).*

(Continued)

*Primary Examiner* — Celia Chang
(74) *Attorney, Agent, or Firm* — Klarquist Sparkman, LLP

(57) ABSTRACT

A number of thalidomide metabolites having superior antiangiogenic properties have now been isolated and identified. In addition, thalidomide analogs that mimic the effects of the isolated and identified active thalidomide metabolites, and variations of such thalidomide analogs, have been developed. Such thalidomide analog compounds show enhanced potency in the inhibition of undesirable angiogenesis without the undesirable effects of administration of thalidomide.

6 Claims, 6 Drawing Sheets

(56) References Cited

FOREIGN PATENT DOCUMENTS

| WO | WO 96/20705 | 7/1996 |
|---|---|---|
| WO | WO 96/20926 | 7/1996 |
| WO | WO 97/12652 | 4/1997 |
| WO | WO 97/23457 | 7/1997 |
| WO | WO 97/37988 | 10/1997 |
| WO | WO 97/45117 | 12/1997 |
| WO | WO 98/03502 | 1/1998 |
| WO | WO 98/19649 | 5/1998 |
| WO | WO 98/25895 | 6/1998 |
| WO | WO 99/13873 | 3/1999 |
| WO | WO 99/58096 | 11/1999 |
| WO | WO 99/59960 | 11/1999 |
| WO | WO 01/74362 | 10/2001 |
| WO | WO 02/064083 | 8/2002 |
| WO | WO 02/068414 A2 | 9/2002 |
| WO | WO 03/014315 | 2/2003 |
| WO | WO 03/097052 | 11/2003 |
| WO | WO 2004/085422 | 10/2004 |
| WO | WO 2005/016325 | 2/2005 |
| WO | WO 2005/016326 | 2/2005 |

OTHER PUBLICATIONS

Shibata et al. "Pnhenylphthimides . . . " chem. Pharm. Bull. v. 44, p. 156-162 (1996).*

Gutschow et al. "Aza analogues . . . " Bioorg. Med. Chem. vo. 9, p. 1059-1065 (2001).*

MPEP 2132, p. 1-2, electronic pages (2013).*

NOT-OD-05-022 "Polucy on enhancing . . . " p. 1-14 (2005).*

Bartlett et al., "Phase I study to determine the safety, tolerability and immunostimulatory activity of thalidomide analogue CC-5013 in patents with metastatic malignant melanoma and other advanced cancers," *British Journal of Cancer* 90:955-961, 2004.

Bauer et al., "Inhibition of Angiogenesis by Thalidomide Requires Metabolic Activation, Which is Species-dependent," *Biochemical Pharmacology* 55:1827-1834, 1998.

Bray et al., "Improved Procedures for the Preparation of (+)—(1R, 2S, 4R)-4-Amino-2-Hydroxy-1-Hydroxymethyl Cyclopentane," *Tetrahedron Letters* 36(25):4483-4486, 1995.

Cava et al., "Thionation Reactions of Lawesson's Reagents," *Tetrahedron* 41(22):5061-5087, 1985.

Ching et al., "Interaction of thalidomide, phthalimide analogues of thalidomide and pentoxifylline with the anti-tumour agent 5,6-dimethylxanthenone-4-acetic acid: concomitant reduction of serum tumour necrosis factor—alpha and enhancement of anti-tumour activity," *British Journal of Cancer* 78(3):336-343, 1998.

Corral et al., "Differential Cytokine Modulation and T Cell Activation by Two Distinct Classes of Thalidomide Analogues That Are Potent Inhibitors of TNF-α," *The Journal of Immunology* 163:380-386, 1999.

D'Amato et al., "Thalidomide is an Inhibitor of Angiogenesis," *Proc. Nat'l. Acad. Sci. USA* 91:4082-4085, 1994.

Davies et al., "Thalidomide (Thal) and Immunomodulatory Derivatives (IMiDs) Augment Natural Killer (NK) Cell Cytotoxicity in Multiple Myeloma (MM)," American Society of Hematology, 42$^{nd}$ Annual Meeting, San Francisco, CA, Dec. 1-5, 2000 (Abstract No. 3617).

Davies et al., "Thalidomide (Thal) and Immunomodulatory Derivatives (IMiDs) Augment Natural Killer (NK) Cell Cytotoxicity in Multiple Myeloma (MM)," VIIIth International Myeloma Workshop, Banff, Canada, May 4-8, 2001 (Abstract No. P222).

Davies et al., "Thalidomide and immunomodulatory derivatives augment natural killer cell cytotoxicity in multiple myeloma," *Blood* 98(1):210-216, 2001.

Dalgleish et al., "Thalidomide Analogues CC-5013 and CC-4047 Induce T cell Activation and IL-12 Production in Patients with Both Solid Tumours and Relapsed and Refractory Multiple Myeloma," *British Journal of Cancer* 88(Suppl. 1)S25-S54 (Abstract P14), 2003.

De et al., "Possible Antineoplastic Agents: III—Synthesis of 6-Alkyl-2-[4'Methoxyphalimido] and 6-Alkyl-3-[3'-4'-Dimethoxyphenyl] Glutarimides," *J. Indian Chem. Soc.* 53:1122-1125, 1976.

De et al., "Possible Antineoplastic Agents: Part IV—Synthesis & Antineoplastic Potency of N-Substituted α-(4,5-Dimethoxyphthalimido)glutarimides & N-Substituted β-)4-Bromophenyl)gludarimides," *Indian J. of Chem.* 16B:510-512, 1978.

Deckers et al., "Effect on Angiogenic and Antiangiogenic Compounds on the Outgrowth of Capillary Structures from Fetal Mouse Bone Explants," *Laboratory Investigation* 81(1):5-15, 2001.

Dibbs et al., "Thalidomide and Thalidomide Analogs Suppress TNFα Secretion by Myocytes," *Circulation* 98(17(Suppl), Abstract No. 1284):I247, 1998.

Dredge et al., "A costimulatory thalidomide analog enhances the partial anti-tumor immunity of an autologous vaccination in a model of colorectal cancer," American Association for Cancer Research, 93$^{rd}$ AnnualMeeting, San Francisco, CA, Apr. 6-10, 2002 (Abstract No. 491).

Dredge et al., "Protective Antitumor Immunity Induced by a Costimulatory Thalidomide Analog in Conjunction with Whole Tumor Cell Vaccination Is Mediated by Increased Th1-Type Immunity," *The Journal of Immunology* 168:4914-4919, 2002.

Dredge et al., "Novel thalidomide analogues display anti-angiogenic activity independently of immunomodulatory effects," *British Journal of Cancer* 87:1166-1172, 2002.

Dredge et al., "Recent developments in antiangiogenic therapy," *Expert Opin. Biol. Ther.* 2(8):953-966, 2002.

Dredge et al., "Immunological Effects of Thalidomide and Its Chemical and Functional Analogs," *Critical Reviews in Immunology* 22(5&6):425-437, 2002.

Dredge et al., "Thalidomide analogs as emerging anti-cancer drugs," *Anti-Cancer Drugs* 14:331-335, 2003.

Dredge et al., "Angiogenesis inhibitors in cancer therapy," *Current Opinion in Investigational Drugs* 4(6):667-674, 2003.

Eisen et al., "Continuous low dose Thalidomide: a phase II study in advanced melanoma, renal cell, ovarian and breast cancer," *British Journal of Cancer* 82(4):812-817, 2000.

Fine et al., "Phase II Trial of the Antiangiogenic Agent Thalidomide in Patients with Recurrent High-Grade Gliomas," *Journal of Clinical Oncology* 18(4):708-715, 2000.

Folkes et al., "Oxidative activation of indole-3-acetic acids to cytotoxic species—a potential new role for plant auxins in cancer therapy," *Biochemical Pharmacology* 61(2):129-136, 2001.

Greig et al., "New Therapeutic Strategies and Drug Candidates for Neurodegenerative Diseases. p53 and TNF-α Inhibitors, and GLP-1 Receptor Agonists," *Ann. N.Y. Acad. Sci.* 1035:290-315, 2004.

Greig et al., "Thalidomide-based TNF-α Inhibitors for neurodegenerative diseases," *Acta Neurobiol Exp* 64(1):1-9, 2004.

Gupta et al., "Adherence of multiple myeloma cells to bone marrow stromal cells upregulates vascular endothelial growth factor secretion: therapeutic applications," *Leukemia* 15:1950-1961, 2001.

Gütschow et al., "Aza analogues of thalidomide: Synthesis and evaluation as inhibitors of tumor necrosis factor-alpha production in vitro" *Bioorganic & Medical Chemistry* 9:1059-1065, 2001.

Hashimoto, "Novel Biological Response Modifier Derived from Thalidomide," *Current Medicinal Chemistry* 5(3):163-178, 1998.

Hashimoto et al., "Structural Development of Biological Response Modifiers Based on Thalidomide," *Bioorganic & Medicinal Chemistry* 10:461-479, 2002.

Haslett et al., "Thalidomide and a Thalidomide Analogue Drug Costimulate Virus-Specific CD8$^+$ T Cells in Vitro," *The Journal of Infectious Diseases* 187:946-955, 2003.

Hayashi et al., "Mechanisms Whereby Immunomodulatory Analogs of Thalidomide Augment Autologous NK Cell Anti-Myeloma Immunity," American Society of Hematology, 44$^{th}$ Annual Meeting, Philadelphia, PA, Dec. 6-10, 2002 (Abstract No. 3219).

He et al., "Synthesis of Thalidomide Analogs and Their Biological Potential for Treatment of Graft Versus Host Disease (GVHD)," American Chemical Society (Abstract No. 216), 1993.

Hernandez-Ilizaliturri et al., "Addition of Immunomodulatory Drugs CC5013 or CC4047 to Rituximab Enhances Anti-Tumor Activity in a Severe Combined Immunodeficiency (SCID) Mouse Lymphoma

(56) References Cited

OTHER PUBLICATIONS

Model," American Society of Hematology, 45th Annual Meeting, San Diego, CA, Dec. 6-9, 2003 (Abstract No. 235).
Hess et al., "Synthesis and immunological activity of water-soluble thalidomide prodrugs," *Bioorganic and Medicinal Chem.* 9(5):1279-1291, 2001.
Hideshima et al., "Thalidomide (Thal) and Its Analogs Overcome Drug Resistance of Human Multiple Myeloma (MM) Cells to Conventional Therapy," American Society of Hematology, 42nd Annual Meeting, San Francisco, CA, Dec. 1-5, 2000 (Abstract No. 1313).
Isner et al., "Therapeutic Angiogenesis," *Frontiers in Bioscience* 3:e49-69, 1998.
Jönsson, "Chemical structure and teratogenic properties," *Acta Pharm. Suecica* 9:521:542, 1972.
Karbownik et al., "Indole-3-propionic acid, a melatonin-related molecule, protects hepatic microsomal membranes from iron-induced oxidative damage: relevance to cancer reduction," *Journal of Cellular Biochemistry* 81(3):507-513, 2001.
Kim et al., "Inhibition of vascular endothelial growth factor-induced angiogenesis suppresses tumour growth in vivo," *Nature* 362:841-844, 1993.
Kumar et al., "Antimyeloma activity of two novel N-substituted and tetraflourinated thalidomide analogs," *Leukemia* 19:1253-1261, 2005.
Lentzsch et al., "S-3-amino-phthalimido-glutarimide inhibits angiogenesis and growth of B-cell neoplasias in mice," *Cancer Research* 62:2300-2305, 2002.
Lentzsch et al., "Immunomodulatory Derivatives of Thalidomide (IMiD CC-4047) Down Regulates CAAT/Enhancer-Binding Protein β(C/EBPβ) in Multiple Myeloma (MM)", American Society of Hematology, 45th Annual Meeting, San Diego, CA, Dec. 6-9, 2003 (Abstract No. 3456).
Lentzsch et al., "Immunomodulatory Derivatives of Thalidomide (IMiD CC-4047) Determine the Lineage Commitment of Hematopoietic Progenitors by Down Regulation of GATA-1 and Modulation of Cytokine Secretion," American Society of Hematology, 45th Annual Meeting, San Diego, CA, Dec. 6-9, 2003 (Abstract No. 3073).
Lepper et al., "Comparative Molecular Field Analysis and Comparative Molecular Similarity Indices Analysis of Thalidomide Analogues as Angiogenesis Inhibitors," *J Medicinal Chem.* 47(9):2219-2227, 2004.
Little et al., "Activity of Thalidomide in AIDS-Related Kaposi's Sarcoma," *Journal of Clinical Oncology* 18(13):2593-2602, 2000.
Luzzio et al., "Thalidomide metabolites and analogs. Part 2: Cyclic derivatives of 2-$N$-phthalimido-2$S$,3$S$ (3-hydroxy) ornithine," *Tetrahedron Letters* 41:7151-7155, 2000.
Luzzio et al., "Thalidomide Metabolites and Analogues. 3. Synthesis and Antiangiogenic Activity of the Teratogenic and TNFα-Modulatory Thalidomide Analogue 2-(2,6-Dioxopiperidine-3-yl)phthalimidine," *Journal of Medicinal Chemistry* 46(18):3793-3799, 2003.
Man et al., "α-Fluoro-Substituted Thalidomide Analogues," *Bioorganic & Medicinal Chemistry Letters* 13:3415-3417, 2003.
Marks et al., "Effects of Putative Hydroxylated Thalidomide Metabolites on Blood Vessel Density in the Chorioallantoic Membrane (CAM) Assay and on Tumor and Endothelial Cell Proliferation," *Biol. Pharm. Bull.* 25(5):597-604, 2002.
Marriott et al., "CC-3052: A Water-Soluble Analog of Thalidomide and Potent Inhibitor of Activation-Induced TNF-α Production," *The Journal of Immunology* 161:4236-4243, 1998.
Marriott et al., "Immunotherapeutic and antitumour potential of thalidomide analogues," *Expert Opin. Biol. Ther.* 1(4):1-8, 2001.
Marriott et al., "Thalidomide and its analogues have distinct and opposing effects on TNF-α and TNFR2 during co-stimulation of both CD4+ and CD8+ T cells," *Clin Exp Immunol* 130:75-84, 2002.
Marriott et al., "A Novel Subclass of Thalidomide Analogue with Anti-Solid Tumor Activity in Which Caspase-dependent Apoptosis is Associated with Altered Expression of bcl-2 Family Proteins," *Cancer Research* 63:593-599, 2003.
Marriott et al., "Thalidomide Derived Immunomodulatory Drugs (IMiDs) as Potential Therapeutic Agents," *Current Drug Targets—Immune, Endocrine & Metabolic Disorders* 3:181-186, 2003.
Meierhofer et al., "New insights into the pharmacological and toxicological effects of thalidomide," *Current Opinion in Drug Discovery & Development* 6(1):92-99, 2003.
Mitsiades et al., "Apoptotic signaling induced by immunomodulatory thalidomide analogs in human multiple myeloma cells: therapeutic implications," *Blood* 99(12):4525-4530, 2002.
Moutouh de Parseval et al., "Novel immunomodulatory drugs (IMiDs®): A potential, new therapy for β-hemoglobinopathies," American Society of Hematology, 46th Annual Meeting, San Diego, CA, Dec. 4-7, 2004 (Abstract No. 3740).
Miyashi et al., "Inducer-Specific Regulators of tumor Necrosis Factor Alpha Production," *Chem. Pharm. Bull.* 44(10):1980-1982, 1996.
Miyashi et al., "Novel Biological Response Modifiers: Phthalimides with Tumor Necrosis Factor-α Production-Regulating Activity," *J. Med. Chem.* 40:2858-2865, 1997.
Muller et al., "Amino-Substituted Thalidomide Analogs: Potent Inhibitors of TNF-α Production," *Bioorganic & Medicinal Chemistry Letters* 9:1625-1630, 1999.
Ng et al., "Antiangiogenic Activity of N-substituted and Tetrafluorinated Thalidomide Analogues," *Cancer Research* 63(12):3189-3194, 2003.
Ng et al., "Antitumor Effects of Thalidomide Analogs in Human Prostate Cancer Xenografts Implanted in Immunodeficient Mice," *Clinical Cancer Research* 10:4192-4197, 2004.
Ni et al., "Experimental study on activity of human recombinant adenovirus vector expressing human endostatin in vitro," *Dier Junyi Daxue Xuebao Bianjibu* 23(3):261-263, 2002 (Abstract only).
Niwayama et al., "Enhanced Potency of Perfluorinated Thalidomide Derivatives for Inhibition of LPS-Induced Tumor Necrosis Factor-α Production is Associated with a Change of Mechanism of Action," *Bioorganic & Medicinal Chemistry Letters* 8:1071-1076, 1998.
Niwayama et al., "Potent Inhibition of Tumor Necrosis Factor-α Production by Tetrafluorothalidomide and Tetrafluorophthalimides," *J. Med. Chem.* 39:3044-3045, 1996.
Neumann et al., "$N$-(Sulfonyloxy)phthalimides and Analogues Are Potent Inactivators of Serine Proteases," *The Journal of Biological Chemistry* 269(34):21561-21567, 1994.
Orzeszko et al., "Tumor necrosis factor-alpha production-regulating activity of phthalimide derivatives in genetically modified murine melanoma cells B78H1," *Il Farmaco* 58:371-376, 2003.
Pagani et al., "Effect of a series of substances related to N-alpha-naphthylphthalamic acid on root geotropism of Lens esculanta Moench s.1. seeds," FRPSX, *Farmaco Ed. Sci.* 25:203-224, 1970.
Patten et al., "The Early Use of the Serum Free Light Chain Assay in Patients with Relapsed Refractory Myeloma Receiving Treatment with a Thalidomide Analogue (CC-4047)," American Society of Hematology, 45th Annual Meeting, San Diego, CA, Dec. 6-9, 2003 (Abstract No. 1640).
Payvandi et al., "The thalidomide analogs IMiDs enhance expression of CD69 stimulatory receptor on natural killer cells," American Association of Cancer Research, 92nd Annual Meeting, New Orleans, LA, Mar. 24-28, 2001 (Abstract No. 1793).
Payvandi et al., "Thalidomide analogs IMiDs inhibit expression of cyclooxygenase-2 in multiple myeloma cell line and LPS stimulated PBMCs," American Society of Hematology, 43rd Annual Meeting, Orlando, FL, Dec. 7-11, 2001 (Abstract No. 2689).
Payvandi et al., "Thalidomide and IMiDs Inhibit Microvessel Formation from Human Arterial Rings in the Absence of Human Liver Microsomes," American Society of Hematology, 44th Annual Meeting, Philadelphia, PA, Dec. 6-10, 2002 (Abstract No. 5046).
Payvandi et al., "CC-5013 inhibits the expression of adhesion molecules ICAM-1 and CD44 and prevents metastasis of B16 F10 mouse melanoma cells in an animal model," American Society of Clinical Oncology, 39th Annual Meeting, Chicago, IL, May 31-Jun. 3, 2003 (Abstract No. 992).
Payvandi et al., "Immunomodulatory drugs inhibit expression of cyclooxygenase-2 from TNF-α, IL-1β, and LPS-stimulated human PBMC in a partially IL-10-dependent manner," *Cellular Immunology* 230:81-88, 2004.

(56) References Cited

OTHER PUBLICATIONS

Pratt et al., "Phthalic Acid Derivatives: Constitution and Color, XIV.[1] Some Derivatives of Tetrabromophthalimide," JACSAT *J. Amer. Chem. Soc.* 40:1420, 1918.

Schafer et al., "Enhancement of Cytokine Production and AP-1 Transcriptional Activity in T Cells by Thalidomide-Related Immunomodulatory Drugs," *The Journal of Pharmacology and Experimental Therapeutics* 305(3):1222-1232, 2003.

Schey et al., "Phase I Study of an Immunomodulatory Thalidomide Analog, CC-4047, in Relapsed or Refractory Multiple Myeloma," *Journal of Clinical Oncology* 22(16):1-8, 2004.

Sedlak et al., "Preparation, 1H and 13C NMR spectra of substituted 2-benzoylaminocarboxamides," *Collection of Czechoslovak Chemical Communications, Academic Press* 60:150-160, 1995.

Shah et al., "Synehesis and Enantiomeric Separation of 2-Phthalimidino-glutaric Acid Analogues: Potent Inhibitors of Tumor Metastasis," *J. Med. Chem.* 42:3014-3017, 1999.

Shaughnessy et al., "Global Gene Expression Analysis Shows Loss of C-MYC and IL-6 Receptor Gene mRNA After Exposure of Myeloma to Thalidomide and IMiD," The American Society of Hematology, 42nd Annual Meeting, San Francisco, CA, Dec. 1-5, 2000 (Abstract No. 2485).

Shimazawa et al., "Antiangiogenic Activity of Tumor Necrosis Factor-α Production Regulators Derived from Thalidomide," *Biol. Pharm. Bull.* 22(2):224-226, 1999.

Shimazawa et al., "Nonpeptide Small-Molecular Inhibitors of Dipeptidyl Peptidase IV:N-Phenylphthalimide Analogs," *Bioorganic & Medicinal Chemistry Letters* 9:559-562, 1999.

Shimazawa et al., "Novel Small Molecule Nonpeptide Aminopeptidase N inhibitors with a Cyclic Imide Skeleton," *J. Enzyme Inhibition* 14:259-275, 1999.

Shire et al., "TNF-α inhibitors and rheumatoid arthritis," *Exp. Opin. Ther. Patents* 8(5):531-544, 1998.

Singhal et al., "Antitumor Activity of Thalidomide in Refractory Multiple Myeloma," *The New England Journal of Medicine* 341(21):1565-1571, 1999.

Singhal et al., "Thalidomide in Cancer. Potential Uses and Limitations," *BioDrugs* 15(3):163-172, 2001.

Streetly et al., "Thalidomide analogue CC-4047 is effective in the treatment of patients with relapsed and refractory multiple myeloma (MM) and induces T-cell activation and IL-12 production," International Multiple Myeloma Workshop, IXth International Conference, Salamanca, Spain, May 23-27, 2003 (Abstract No. 367).

Streetly et al., "An Update of the Use and Outcomes of the New Immunomodulatory Agent CC-4047 (Actimid) in Patients with Relapsed/Refractory Myeloma," American Society of Hematology, 45th Annual Meeting, San Diego, CA, Dec. 6-9, 2003 (Abstract No. 829).

Streetly et al., "Changes in Neutrophil Phenotype Following the Administration of CC-4047 (Actimid) to Patients with Multiple Myeloma," American Society of Hematology, 45th Annual Meeting, San Diego, CA, Dec. 6-9, 2003 (Abstract No. 2543).

Suzuki, et al., "Use of a new protecting group in an attempted synthesis of cyclopropyldihydroxyphenylalanine," *Journal of Organic Chemistry* 48(24):4769-4771, 1983.

Teo et al., "Chiral Inversion of the Second Generation IMiD™ CC-4047 (ACTIMID™) in Human Plasma and Phosphate-Buffered Saline," *Chirality* 15:348-351, 2003.

Teubert et al., "5'-Substituted Thalidomide Analogues as Modulators of TNF-α," *Arch. Pharm. Pharm. Med. Chem.* 331:7-12, 1998.

"The Merck Index," Merck & Co. 2001.

Tsenova et al., "Use of IMiD3, a Thalidomide Analog, as an Adjunct to Therapy for Experimental Tuberculous Meningitis," *Antimicrobial Agents and Chemotherapy* 46(6):1887-1895, 2002.

Tweedie et al., "TNF-α Synthesis Inhibitors on the 3-Phthalimidoglutarimide Backbone as Therapeutic Candidates for Neurodegenerative Diseases," 7th *International Conference on Alzheimer's and Parkinson's Disease*, pp. 77-86, Sorrento, Italy, Mar. 9-13, 2005.

Understanding Angiogenesis "About Angiogenesis," Angiogenesis Foundation from the website, 2005.

Weinz et al., "Investigation of the in vitro biotransformation and simultaneous enantioselective separation of thalidomide and its neutral metabolites by capillary electrophoresis," *Journal of Chromatography B* 674:287-292, 1995.

Ye et al., "Novel IMiD Drugs Enhance Expansion and Regulate Differentiation of Human Cord Blood CD34+ Cells with Cytokines," American Society of Hematology, 44th Annual Meeting, Philadelphia, PA, Dec. 6-10, 2002 (Abstract No. 4099).

Zeldis et al., "Potential New Therapeutics for Waldenstrom's Macroglobulinemia," *Seminars in Oncology* 30(2):275-281, 2003.

Zeldis et al., "Update on the evolution of the IMiD™," International Society for Biological Therapy of Cancer, 18th Annual Meeting, Bethesda, MD, Oct. 30-Nov. 2, 2003 (Oral Abstract).

Zhang et al., "CC-5079, a novel microtubule and TNF-a inhibitor with anti-angiogenic and antimetastasis activity," American Association for Cancer Research, National Cancer Institute, and European Organization for Research and Treatment of Cancer, International Conference on Molecular Targets and Cancer Therapeutics, Boston, MA, Nov. 17-21, 2003 (Abstract No. B012).

Zhang et al., "Preparation of water-soluble thalidomide derivatives," Database CA Online, Chemical Abstracts Service, Database Accession No. 2004:817880, 2004 (Abstract).

Zhu et al., "Thiothalidomides: Novel Isosteric Analogues of Thalidomide with Enhanced TNF-α Inhibitory Activity," *J. Med. Chem.* 46(24):5222-5229, 2003.

Shibata et al., "Phenylphthalimides with Tumor Necrosis Factor Alpha Production-Enhancing Activity," *Chem. Pharm. Bull.* 44(1):156-162, Jan. 1996.

\* cited by examiner

ANALOGS OF THALIDOMIDE AS POTENTIAL ANGIOGENESIS INHIBITORS

PRIORITY CLAIM

This is a continuation of U.S. patent application Ser. No. 10/469,359, filed Nov. 14, 2003, which is a §371 U.S. national stage of PCT/US02/05868, filed Feb. 26, 2002, which was published in English under PCT Article 21(2), and claims the benefit of U.S. Provisional Application No. 60/271,941, filed Feb. 27, 2001, all of which are incorporated by reference in their entirety.

FIELD OF THE INVENTION

The present invention concerns anti-angiogenesis compositions and methods, and particularly thalidomide analogs that actively inhibit angiogenesis in humans and animals.

BACKGROUND OF THE INVENTION

Angiogenesis is the formation of new blood vessels from pre-existing vessels. Angiogenesis is prominent in solid tumor formation and metastasis. A tumor requires formation of a network of blood vessels to sustain the nutrient and oxygen supply for continued growth. Some tumors in which angiogenesis is important include most solid tumors and benign tumors, such as acoustic neuroma, neurofibroma, trachoma, and pyogenic granulomas. Prevention of angiogenesis could halt the growth of these tumors and the resultant damage due to the presence of the tumor.

It has been shown that there is a direct correlation between tumor microvessel density and the incidence of metastasis. Tumor cells themselves can produce factors that stimulate the proliferation of endothelial cells and new capillary growth. Angiogenesis is important in two stages of tumor metastasis. The first stage where angiogenesis stimulation is important is in the vascularization of the tumor, which allows tumor cells to enter the blood stream and to circulate throughout the body. After the tumor cells have left the primary site, and have settled into the secondary, metastasis site, angiogenesis must occur before the new tumor can grow and expand. Therefore, prevention of angiogenesis could lead to the prevention of metastasis of tumors and possibly contain the neoplastic growth at the primary site. These observations have led to the investigation of anti-angiogenic agents as possible therapeutic options for various cancers.

In the 1950's, thalidomide was marketed as a sedative in Europe but was withdrawn from the market when it was found to be a potent teratogen. Recently, thalidomide has been promoted as a possible inhibitor of angiogenesis. Studies have indicated, however, that thalidomide itself is not sufficiently active to inhibit angiogenesis. Instead, the anti-angiogenic activity or effects previously attributed to thalidomide are the resulting effects of compounds that are only present following metabolic activation of thalidomide (i.e., "active" thalidomide metabolites). D'Amato, R.; Loughman Flynn, E.; Folkman, J., Thalidomide as an Inhibitor of Angiogenesis. *Proc. Nat'l. Acad. Sci.*, 1994, 91, 4082-4085; M.; Bauer, K.; Dixon, S.; Figg, W. Inhibition of Angiogenesis by Thalidomide Requires Metabolic Activation, Which Is Species-dependent. *Biochem. Pharmacology*, 1998, 55, 1827-1834. Accordingly, it has been speculated that certain metabolites of thalidomide rather than thalidomide itself are responsible for its anti-angiogenic properties. However, the specific thalidomide metabolites responsible for the anti-angiogenic properties have not yet been isolated and identified.

There are hundreds, if not thousands of compounds formed as a result of metabolism of thalidomide and the actively metabolized products of hydrolysis compounds of the thalidomide. Many of the thalidomide metabolites are inactive and/or unstable. There is no way to predict which metabolite(s) will have superior anti-angiogenic properties. As such, "active" thalidomide metabolites (or "active" thalidomide analogs) having superior anti-angiogenic properties are not yet available.

If the anti-angiogenic activity can be attributed to one or a small number of thalidomide metabolites and those metabolites could be isolated and identified, then active thalidomide analogs may be synthesized to provide exceptionally effective compounds inhibiting angiogenic effects. This is especially true when comparing thalidomide to "active" thalidomide analogs. To obtain such active compounds from thalidomide, thalidomide must first be activated via metabolism; only a very small amount of thalidomide would actually be metabolized to one or more "active" metabolites. Further, it may be possible to administer such "active" thalidomide analogs in lower amounts and still achieve the desired anti-angiogenic effects. Moreover, such "active" thalidomide analogs could be safer than thalidomide in avoiding undesirable side effects, e.g., teratogenicity or neurotoxicity, and may be more specific to tumor angiogenesis than thalidomide-thalidomide has a host of undesirable biological activities.

Accordingly, there is a need for isolation and identification of the thalidomide metabolites having superior anti-angiogenic properties. Further, there is a need for the synthesis of purified thalidomide analogs that can mimic the effects of the isolated and identified thalidomide metabolites that display such anti-angiogenic activity. In addition, there is a need for a method for treating undesired angiogenesis using such active thalidomide analogs.

SUMMARY OF THE INVENTION

The present invention provides compounds having superior anti-angiogenic properties. More specifically, a number of thalidomide metabolites having superior anti-angiogenic properties have now been isolated and identified. Accordingly, the present invention provides active thalidomide analogs that mimic the effects of the isolated and identified active thalidomide metabolites, and variations of such thalidomide analogs. Such thalidomide analog compounds of the present invention show enhanced potency in the inhibition of undesirable angiogenesis.

The present method further provides for inhibiting unwanted angiogenesis in a human or animal by administering to the human or animal with the undesired angiogenesis a composition comprising an effective amount of active thalidomide analog of the present invention. Specifically, the invention includes a method of inhibiting angiogenesis by exposing the mass having the undesirable angiogenesis to an angiogenesis inhibiting amount of one or more of the present invention thalidomide analogs (and variations of the same) or pharmaceutically acceptable salts of such compounds, wherein such thalidomide analogs (and variations of the same) have the following general formula (Formula A):

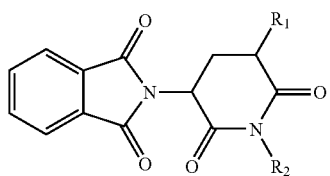

(A)

wherein R1 is a hydrogen when R2 is methyl alcohol, a branched or unbranched alkyl alcohol, alkyl acid or amino acid, alkylamine, substituted cycloalkyl, substituted alkylphenyl, or phenylalkyl or R1 is a hydroxyl group, a substituted or unsubstituted cycloalkyl aryl or heteroaryl when R2 is a hydrogen, methyl alcohol, a branched alkylalcohol, alkyl acid, amino acid, alkylamino, substituted cycloalkyl, substituted phenylalkyl or alkylphenyl. Additionally, the phthalimid moiety may be replaced by bicyclo [2,2,1]hepten-icarboxylicimid.

In another embodiment the thalidomide analogs (and variations of the same) have the following general formula (Formula B):

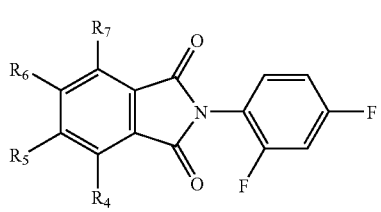

(B)

wherein R4 through R7 are fluoride or are another halogen, R4 through R7 may comprise the same or different halogens or R5 and R6 are hydrogen and R4 and R7 are methyl groups. Alternatively, there may be substitutions on the isoindole ring, e.g., R4 through R7 may comprise different groups on the isoindole ring to obtain 4-chloro; 4-nitro; 5,6-dichloro; 4-methyl; 5-methyl; 5,6-dimethyl; and 4,5,6,7-tetrachloro. Further, the isoindole ring may be replaced with succinimides or maleimides. Additionally, other halogens may be substituents at the phenyl ring. For example, rather than 2,4-fluoro, the following groups may be substituents on the phenyl ring: 2,3-difluoro; 2,5-difluoro; 2,6-difluoro; 3,4-difluoro; 3,5-difluoro; 2,3-dichloro; 2,4-dichloro; 2,4-dichloro; 2,6-dichloro; 2,4-dibromo; 2,5-dibromo; 2,6-dibromo; 2-fluoro; 3-fluoro; 4-fluoro; 2-chloro; 3-chloro; 4-chloro; 2-bromo; 3-bromo; 4-bromo; 2,3,4-trifluoro. Additionally, the phthalimid moiety may be replaced by bicyclo [2,2,1]hepten-icarboxylicimid.

In another aspect of the invention, the thalidomide analogs (and variations of the same) have the following general formula (Formula C):

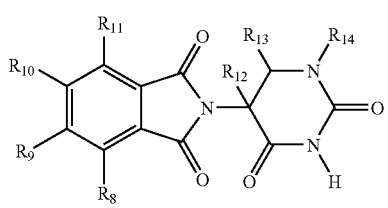

(C)

wherein R8 through R11 are hydrogen, R12 is an alkyl residue, R13 is a double-bonded oxygen, sulfur or nitrogen, and R14 is an alkyl, cycloalkyl, substituted phenyl, or a cyclic alkyl, such as cyclo-hexane or wherein R8 through R11 are fluoride or are one or more other halogens, R12 is an alkyl residue, R13 is a double-bonded oxygen, sulfur or nitrogen and R14 is benzene or wherein R8 through R11 are fluoride or are one or more other halogens, and R12 through R14 are hydrogen. In addition, the N—H may be substituted by R15, wherein R15 is an alkylamine, substituted cycloalkyl, substituted alkylphenyl or phenylalkyl, methyl alcohol, branched or unbranched alkyl alcohol, alkyl acid or amino acid.

The invention also includes pharmaceutical compositions that include one or more of the compounds of the present invention, or pharmaceutically acceptable salts thereof, and pharmaceutically acceptable carriers. Further, it is to be understood that the compounds included as part of the present invention shown generally in Formulas A-C above, but include all other compounds that are members of the genus described by such general formulas.

Examples of a couple specific thalidomide analog compounds (having superior anti-angiogenic activity) that are members of the genus of Formula A of the present invention are

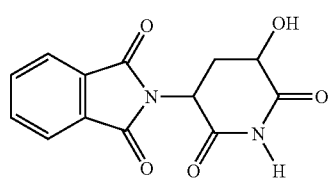

(CPS3)

i.e., 2-(5-hydroxy-2,6-dioxo-piperidin-3-yl)-1H-isoindole-1,3[2H]-dione, and

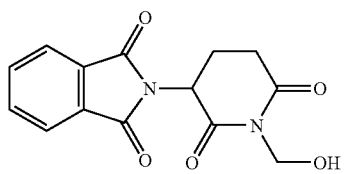

(CPS11)

i.e., 2-(1-hydroxymethyl-2,6-dioxo-piperidin-3-yl)-1,3-dihydro-2H-isoindole-1,3-dione.

Examples of some specific thalidomide analog compounds (having superior anti-angiogenic activity) that are members of the genus of Formula B of the present invention are

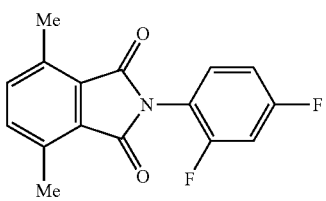

(CPS42)

i.e., 2-(2,4-difluorophenyl)-4,7-dimethyl-1H-isoindole-1,3(2H)-dione, and

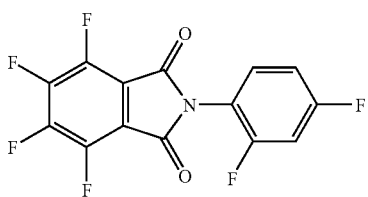

i.e., 2-(2,4-difluorophenyl)-4,5,6,7-tetrafluoro-1H-isoindole-1,3(2H)-dione.

Examples of specific thalidomide analog compounds (having superior anti-angiogenic activity) that are members of the genus of Formula C of the present invention are

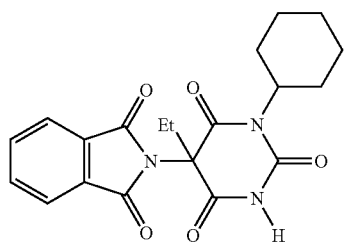

i.e., 1-cyclohexyl-5-ethyl-phthalimidobarbituric acid, and

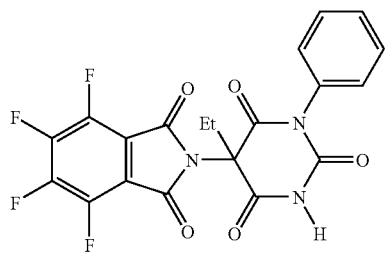

i.e., 5-ethyl-1-phenyl-5-(tetrafluorophthalimido)barbituric acid, and

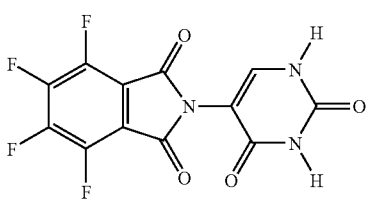

i.e., 5-(tetrafluorophthalimido)pyrimidine-2,4(1H,3H)-dione.

The invention also includes pharmaceutical compositions that include one or more of the above-described compounds.

The foregoing and other objects, features, and advantages of the invention will become more apparent from the following detailed description of particular examples that proceed with reference to the accompanying figures.

DETAILED DESCRIPTION OF PARTICULAR EXAMPLES

Definitions

Figure 1:
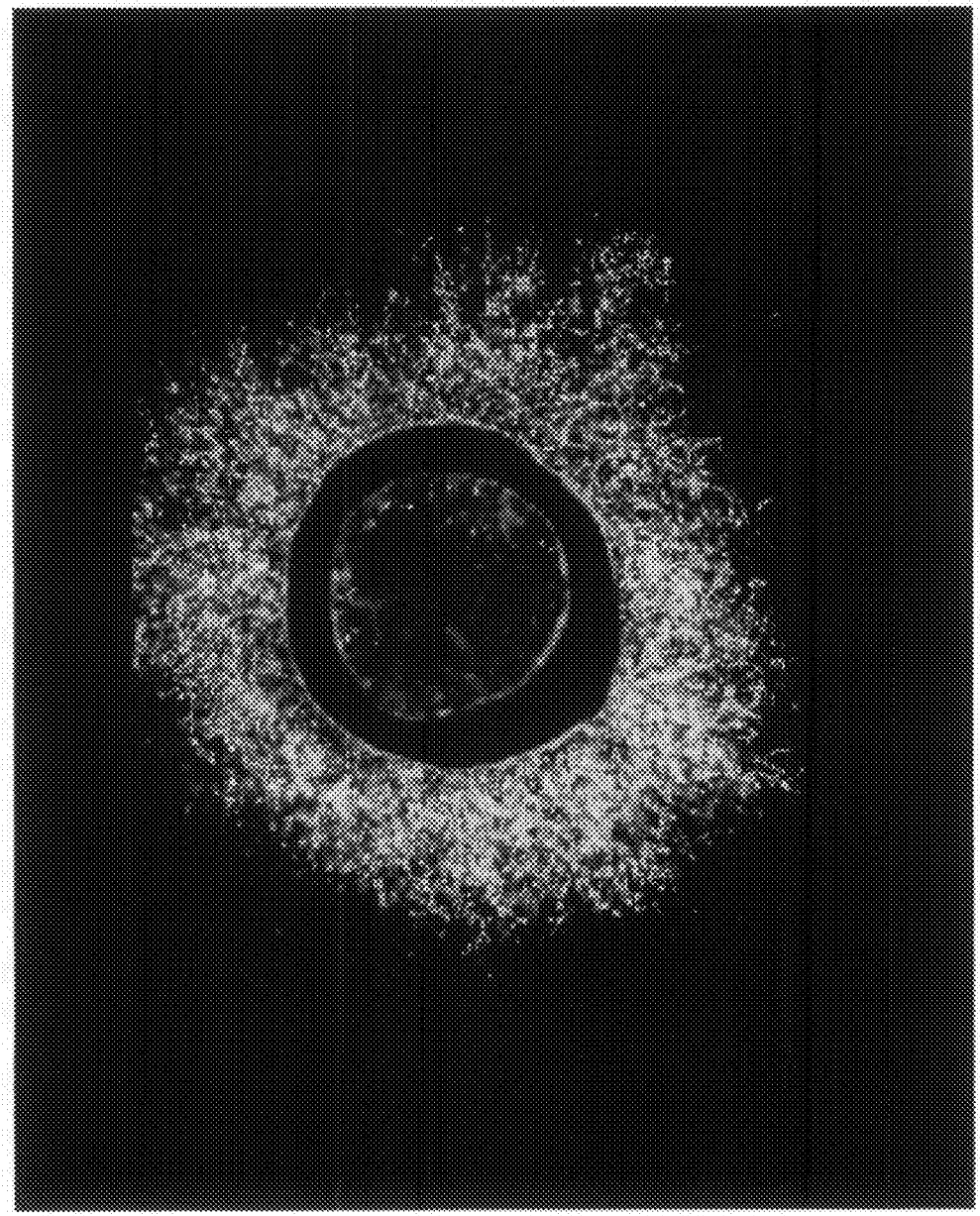
FIG. 1 is a photomicrograph of a control comprising a rat aorta ring treated with DMSO.

The term "halogen" refers to fluoro, bromo, chloro and iodo substituents.

A "pharmaceutical agent" or "drug" refers to a chemical compound or composition capable of inducing a desired therapeutic or prophylactic effect when properly administered to a subject.

The pharmaceutically acceptable salts of the compounds of this invention include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof.

All chemical compounds include both the (+) and (−) stereoisomers, as well as either the (+) or (−) stereoisomer.

A thalidomide "analog" as used herein is a synthetic chemical compound using the thalidomide structure as a backbone (i.e., side groups have been added or such groups have been deleted from the parent structure). The analog differs in structure from thalidomide and its metabolite compounds such as by a difference in the length of an alkyl chain, a molecular fragment, by one or more functional groups, or a change in ionization. Thalidomide analogs generally are not naturally occurring compounds. That is, thalidomide analogs generally cannot be enzymatically or nonenzymatically formed in the body by administration of thalidomide.

A thalidomide "metabolite" is a thalidomide derivative that is formed by enzymatic action, i.e., metabolism of thalidomide in the body. The metabolite is formed by phase-one reactions (e.g., oxidation, reduction, and hydrolysis) or by phase-two reactions (e.g., conjugations). Thalidomide metabolites require an enzyme reaction to be produced.

"Angiogenesis" refers to the development of blood vessels. Accordingly, "anti-angiogenic activity" refers to the inhibition and/or complete cessation of angiogenesis.

"Tumor" refers to a mass of cells resulting from excessive cellular multiplication.

The term "halogen" refers to fluoro, bromo, chloro and iodo substituents.

The term "alcohol" refers to any member of a class of organic compounds in which a hydrogen atom of a hydrocarbon has been replaced by a hydroxy (—OH) group. Unless otherwise mentioned, such an alcohol contains one to twelve carbon atoms.

The term "acid" refers to a compound capable of transferring a hydrogen atom in solution.

The term "alkyl" refers to a cyclic, branched, or straight chain alkyl group containing only carbon and hydrogen, and unless otherwise mentioned contains one to twelve carbon atoms. This term is further exemplified by groups such as methyl, ethyl, n-propyl, isobutyl, t-butyl, pentyl, pivalyl, heptyl, adamantyl, and cyclopentyl. Alkyl groups can either be unsubstituted or substituted with one or more substituents, e.g., halogen, alkyl, alkoxy, alkylthio, trifluoromethyl, acyloxy, hydroxy, mercapto, carboxy, aryloxy, aryloxy, aryl, arylalkyl, heteroaryl, amino, alkylamino, dialkylamino, morpholino, piperidino, pyrrolidin-1-yl, piperazin-1-yl, or other functionality.

The term "amino acid" refers to any of the organic compounds that contain one or more basic amino groups (—NH$_2$) and one or more acidic carboxyl groups (—COOH) and that are polymerized to form peptides and proteins.

The term "aryl" refers to a monovalent unsaturated aromatic carbocyclic group having a single ring (e.g., phenyl) or multiple condensed rings (e.g., naphthyl or anthryl), which can optionally be unsubstituted or substituted with, e.g., halogen, alkyl, alkoxy, mercapto (—SH), alkylthio, trifluoromethyl, acyloxy, hydroxy, mercapto, carboxy, aryloxy, aryl, arylalkyl, heteroaryl, amino, alkylamino, dialkylamino, morpholino, piperidino, pyrrolidin-1-yl, piperazin-1-yl, or other functionality.

The term "alkyl residue" refers to a branched or straight chain alkyl group containing only carbon and hydrogen, and unless otherwise mentioned contains one to twelve carbon atoms. The term is further exemplified by groups such as methyl, ethyl, n-propyl, isobutyl, pentyl, pivalyl and heptyl. Alkyl groups can either be substituted or unsubstituted.

Other chemistry terms herein are used according to conventional usage in the art, as exemplified by *The McGraw-Hill Dictionary of Chemical Terms* (1985), *The Condensed Chemical Dictionary* (1981), and *Dorland's Illustrated Medical Dictionary* (1974).

A "mammal" includes both human and non-human mammals. Similarly, the term "subject" includes both human and veterinary subjects.

An "animal" is a living multicellular vertebrate organism, a category that includes, for example, mammals and birds.

"Thalidomide" or N-(2,6-dioxopiperidin-3-yl)phthalimide has the following chemical structure:

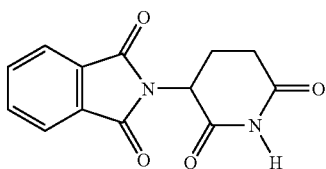 [SMILES: O=C1CCC(N2C(=O)c3ccccc3C2=O)C(=O)N1]

Materials and Methods

Where necessary, solvents were dried and purified according to the recommended procedures. Organic solutions were dried over NaSO$_4$. Evaporation refers to removal of solvent on a Vacuubrand rotary evaporator under reduced pressure of from about 200 to about 15 mbar. Melting points were determined using a Boetius apparatus and are uncorrected. $^1$H NMR spectra (300 Mhz), $^{13}$C NMR spectra (75 MHz), and $^{19}$F spectra (188 MHz) were recorded on a Varian Gemini 300 spectrometer with tetramethylsilane as internal standard; the values of chemical shifts (δ) are given in ppm and coupling constants (J) in Hz. Mass spectral data were determined by direct insertion at 70 eV with a Varian MAT CH6 spectrometer as well as a HP-MS Engine 5989A. Yields refer to purified products and are not optimized.

Compound Reference Numbers

Compounds are identified throughout this detailed description using alpha-numeric references in bold, which correspond to the identification of the compounds as set forth in the Summary of the Invention, and in the following examples.

EXAMPLE 1

Synthesis of and Analytical Results for 2-(5-hydroxy-2,6-dioxo-piperidin-3-yl)-1H-isoindole-1,3 [2H]-dione (CPS3)

This example illustrates the preparation of 2-(5-hydroxy-2,dioxo-piperidin-3(2H)-dione) having a molecular weight of about 274.2. A mixture of about 1.0 g (about 3.2 mmol) of acetic acid 5-(1,3-dioxo-1,3-dihydro-isoindol-2-yl)-2,6-dioxo-piperidin-3-yl-ester (single diastereomer) prepared according to Teubert, U. et al., *Arch. Pharm. Pharm. Med. Chem.*, 1998, 331, 7 (incorporated herein by reference) and about 0.3 g (about 1.6 mmol) of p-toluenesulfonic acid was refluxed in about 30 ml of methanol for about 5 hours. The solution was allowed to cool to about room temperature. After cooling, the precipitated product was filtered and recrystallized from acetone/petroleum ether (having a boiling point of about 60° to about 80° C.). Alternatively, the precipitated, filtered product was recrystallized from acetonitrile. A yield of about 0.52 g (about a 60% yield) of 2-(5-hydroxy-2,6-dioxo-piperidin-3-yl)-1H-isoindole-1,3[2H]-dione having a melting point of about 195° to about 230° C. resulted.

The $^1$H NMR spectral analysis results were as follows: (DMSO-d6) 2.27-2.53 (m, 2H, 4'-H), 4.53-4.57 (m, 1H, 5'-H), 5.29 (dd, J=13.1, 5.2 Hz, 1H, 3'-H), 5.82 (d, J=6.0 Hz, 1H, OH), 7.90-7.94 (m, 4H, aromatic H), 11.22 (s, 1H, NH). The $^{13}$C NMR spectral analysis results were as follows: (DMSO-d6) 31.3 (C-4'), 48.22 (C-3'), 66.33 (C-5'), 123.29, 131.19, 138.88 (C-aromatic), 166.86, 176.17, 169.70, 174.71 (C=O). Mass spectrometry analysis (EI) results yielded, m/z (relative intensity), 274 (13)[M+].

EXAMPLE 2

Synthesis of and Analytical Results for 2-(1-hydroxymethyl-2,6-dioxo-piperidin-3-yl)-1,3-dihydro-2H-isoindole-1,3-dione (CPS11)

This example illustrates the preparation and analysis of 2-(1-hydroxymethyl-2,6-dioxo-piperidin-3-yl)-1,3-dihydro-2H-isoindole-1,3-dione having a molecular weight of about 288.25.

A suspension of about 12.9 g (about 50 mmol) of rac-thalidomide in about 100 mL of an about 35% aqueous formaldehyde solution was refluxed until dissolved. The solution was then allowed to cool to room temperature. After about 24 hours, the precipitate was collected by filtration and washed with about 3% aqueous formaldehyde solution and was then dried with $Na_2SO_4$. A yield of about 10.1 g (about a 70% yield) of 2-(1-hydroxymethyl-2,6-dioxo-piperidin-3-yl)-1,3-dihydro-2H-isoindole-1,3-dione having a melting point of about 165° C. resulted.

The $^1H$ NMR spectral analysis results were as follows: (DMSO-d6) 2.16-2.67 (m, 2H, 4'-H), 2.87-3.11 (m, 2H, 5'-H), 5.08 (d, J=7.2 Hz, 2H, $NCH_2OH$), 5.52 (m, 1H, $CHCH_2$), 6.17 (t, Jab=7.2 Hz, Jbc=7.2 Hz, 1H, OH), 7.92 (s, 4H, Harom.). Analytical values for the compound $C_{14}H_{12}N_2O_5$ were carbon about 58.27%, hydrogen about 4.09%, and nitrogen about 9.52%.

EXAMPLE 3

Synthesis of and Analytical Results for 2-(2,4-difluorophenyl)-4,7-dimethyl-1H-isoindole-1,3(2H)-dione (CPS42)

This example illustrates the preparation and analysis of 2-(2,4-difluorophenyl)-4,7-dimethyl-1H-isoindole-1,3(2H)-dione having an exact mass of 287.08, a molecular weight of about 287.6 (carbon about 66.90%, hydrogen about 3.86%, fluoride about 13.23%, nitrogen about 4.88%, and oxygen about 11.14%).

A mixture of about 2 g (about 15.5 mmol) of 2,4-difluoroaniline, about 2.46 g (about 14 mmol) of 3,6-dimethylphthalic anhydride, and about 100 mL of glacial acetic acid was refluxed for about 3.5 hours. The 3,6-dimethylphthalic anhydride was prepared according to Newman, M. S.; Lord, B. T., *J. Am. Chem. Soc.*, 1944, 66, 733, which is incorporated herein by reference.

The solvent was evaporated to dryness under reduced pressure of from about 200 to about 15 mbar. The residue was dissolved in about 150 mL of $CH_2C_{12}$. The solution was washed three times with about 50 mL of about 0.1 M HCl and twice with about 50 mL of $H_2O$ and was then dried with $Na_2SO_4$. After removal of the solvent, the residue was recrystallized from ethyl alcohol to yield about 1.27 g (32%) 2-(2,4-difluorophenyl)-4,7-dimethyl-1H-isoindole-1,3(2H)-dione having a melting point of about 212° to about 212.5° C.

The $^1H$ NMR spectral analysis results were as follows: (DMSO-d6) 2.59 (s, 6H), 7.24-7.32 (m, 1H), 7.46-7.56 (m, 1H), 7.54 (s, 2H) 7.56-7.66 (m, 1H). The $^{13}C$ NMR spectral analysis results were as follows: (DMSO-d6) 16.87 ($CH_3$), 104.93 (dd, 2J=27.1, 24.2 Hz, C-3'), 112.08 (dd, 2J=22.6, 4J=3.6 Hz, C-5'), 115.93 (dd, 2J=13.2, 4J=3.9 Hz, C-1'), 128.15 (C-4, C-7), 132.07 (dd, 3J=10.1, 2.1 Hz, C-6') 135.37 (C-3a, C-7a), 136.62 (C-5, C-6), 157.81 and 162.08 (d, J=264.1 Hz and d, J=235.6 Hz, C-2' and C-4'), 166.64 (C-1, C-3). Mass spectrometry analysis (EI) results yielded, m/z (relative intensity), 287 (M+, 100), 259 (81c). Analytically calculated values for the compound $C_{16}H_{11}NO_2F_2$ were carbon 66.90%, hydrogen 3.86%, and nitrogen 4.88%. As determined from the NMR and mass spectrometry analysis result values for the compound $C_{16}H_{11}NO_2F_2$ were carbon about 67.20%, hydrogen about 3.77%, and nitrogen about 4.59%.

EXAMPLE 4

Synthesis of and Analytical Results for 1-cyclohexyl-5-ethyl-5-phthalimidobarbituric acid (CPS44)

This example illustrates the preparation and analysis of 1-cyclohexyl-5-ethyl-5-phthalimidobarbituric acid ($C_{20}H_{21}N_3O_5$) having an exact mass of 283.15 and a molecular weight of about 383.4 (carbon about 62.65%, hydrogen about 5.52%, nitrogen about 10.96%, and oxygen about 20.87%). The same compound might alternatively be named, e.g., 1-cyclohexyl-5-(1,3-dioxo-1,3-dihydro-isoindol-2-yl)-5-ethyl-pyrimidine-2,4,6(1H,3H,5H)-trione or 1-cyclohexyl-5-(1,3-dioxo-1,3-dihydro-isoindol-2-yl)-5-ethyl-pyrimidine-2,4,6-trione.

A mixture of about 500 mg (about 2 mmol) of 5-amino-1-cyclohexyl-5-ethylbarbituric acid available from 5-azido-1-cyclohexyl-5-ethylbarbituric acid as described in Guetschow, M. et al., *Synthesis*, 1999, 410-414 (incorporated herein by reference) and about 300 mg (about 2 mmol) of phthalic anhydride and about 20 mL of glacial acetic acid was refluxed for about 5 hours. The mixture was cooled to room temperature and the precipitate was filtered off. The precipitate was next washed with $H_2O$ and dried to give about 470 mg of 1-cyclohexyl-5-ethyl-5-phthalimidobarbituric acid (a yield of about 61%). The 1-cyclohexyl-5-ethyl-5-phthalimidobarbituric acid had a melting point of about 248 to about 253° C.

The $^1H$ NMR spectral analysis results were as follows: (DMSO-$d_6$)* 0.99 (t, 3H, J=7.4 Hz), 1.01-2.21 (m, 10H), 2.68 (q, 2H, J=7.4 Hz), 4.13-4.29 (m, 1H), 7.90 (s, 4H), 12.09 (s, 1H). The $^{13}C$ NMR spectral analysis results were as follows: (DMSO-$d_6$)* 9.10, 24.83, 25.62, 25.71, 27.23, 27.92, 29.05, 54.66, 67.83, 123.74, 130.32, 135.56, 149.24, 167.20, 167.79, 168.28. The mass spectral (EI) analysis results were as follows: m/z (relative intensity) 383 (M+, 5), 302 (M+, 100), 105 (52). Analytically calculated values for the compound $C_{20}H_{21}N_3O_5$ were carbon 62.65%, hydrogen 5.52%, and nitrogen 10.96%. As determined from the NMR and mass spectrometry analysis results values for the compound $C_{20}H_{21}N_3O_5$ were carbon about 62.30%, hydrogen about 5.85%, nitrogen about 10.89%, and oxygen about 20.87%.

EXAMPLE 5

Synthesis of and Analytical Results for 5-ethyl-1-phenyl-5-(tetrafluorophthalimido)barbituric acid (CPS45)

This example illustrates the preparation and analysis of 5-ethyl-1-phenyl-5-(tetrafluorophthalimido)barbituric acid ($C_{20}H_{11}N_3O_5F_4$) having an exact mass of 377.10 and a molecular weight of about 377.4 (carbon about 63.66%, hydrogen about 4.01%, nitrogen about 11.14%, and oxygen about 21.20%). The same compound might alternatively be named, e.g., 5-(1,3-dioxo-1,3-dihydro-4,5,6,7-tetrafluoro-isoindol-2-yl)-5-ethyl-1-phenyl-pyrimidine-2,4,6-(1H,3H, 5H)-trione.

A mixture of about 250 mg (about 1 mmol) of 5-amino-5-ethyl-1-phenylbarbituric acid, about 260 mg (about 1.2 mmol) of tetrafluorophthalic anhydride, and about 7 mL of acetic acid was refluxed for about 3 hours. The solvent was evaporated to dryness under reduced pressure of from about 200 to about 15 mbar. The residue was recrystallized from ethyl alcohol to yield about 270 mg 5-ethyl-1-phenyl-5-(tetrafluorophthalimido)barbituric acid (a 60% yield) having a melting point of about 218° to about 220° C.

The $^1H$ NMR spectral analysis results were as follows: (DMSO-d6), 1.09 (t, 3H, J=7.2 Hz), 2.86 (q, 2H, J=7.3 Hz), 7.20-7.32 (m, 2H), 7.45-7.59 (m, 3H). The $^{13}C$ NMR spectral analysis results were as follows: (DMSO-d6), 9.36, 26.90, 68.10, 112.20, 112.65, 128.05, 128.56, 129.27, 133.91, 141.10, 147.05, 148.88, 162.51, 166.85, 167.18. The mass spectral (EI) analysis results were as follows: m/z (relative intensity), 449 (M+, 62), 421 (M+, 20), 230 (39), 176 (70), 119 (100). Analytically calculated values for the compound $C_{20}H_{11}N_3O_5F_4$ were carbon 53.46%, hydrogen 2.47%, and nitrogen 9.35%. As determined from the NMR and mass spectrometry analysis results values for the compound $C_{20}H_{11}N_3O_5F_4$ were carbon about 53.26%, hydrogen about 2.78%, oxygen about 21.20%, and nitrogen about 9.04%.

EXAMPLE 6

Synthesis of and Analytical Results for 5-(tetrafluorophthalimido)pyrimidine-2,4(1H,3H)-dione (CPS48)

This example illustrates the preparation and analysis of 5-(tetrafluorophthalimido)pyrimidine-2,4(1H,3H)-dione ($C_{12}H_3F_4N_3O_4$) having an exact mass of 329.01 and a molecular weight of about 329.2 (carbon about 43.79%, hydrogen about 0.92%, fluoride about 23.09%, nitrogen about 12.7%, and oxygen about 19.44%). The same compound might alternatively be named, e.g., 2-(2,4-dioxo-1,2,3,4-tetrahydro-pyrimidin-5-yl)-4,5,6,7-tetrafluoro-1H-isoindole-1,3(2H)-dione.

A mixture of about 440 mg anhydride (about 2 mmol) of tetrafluorophthalic, about 254 mg (about 2 mmol) of 5-aminouracil, and about 50 mL of glacial acetic acid was refluxed for about 6 hours. The solution was allowed to cool to about room temperature. After cooling, the precipitated product was filtered, washed with water, and dried with $Na_2SO_4$ to yield about 260 mg (about 40%) of 5-(tetrafluorophthalimido)pyrimidine-2,4(1H,3H)-dione with a melting point of about 3500 to about 355° C.

The $^1$H NMR spectral analysis results were as follows: (DMSO-d6) 7.89 (d, 1H, J=6.2 Hz), 11.47 (d, 1H, J=6.2 Hz), 11.72 (s, 1H). The $^{19}$F NMR spectral analysis results were as follows: (DMSO-d6/CFCl3) −142.0 (m, 2F), −136.5 (m, 2F). The mass spectral (EI) analysis results were as follows: m/z (relative intensity), 329 (M$^+$, 50), 176 (100). Analytically calculated values for the compound $C_{12}H_3F_4N_3O_4$ were carbon about 43.79%, hydrogen about 0.92%, and nitrogen about 12.77%. As determined from the NMR and mass spectrometry analysis result values for the compound $C_{12}H_3F_4N_3O_4$ were carbon about 43.60%, hydrogen about 1.16%, nitrogen about 12.50%.

EXAMPLE 7

Synthesis of and Analytical Results for (CPS49) 2-(2,4-difluoro-phenyl)-4,5,6,7-tetrafluoro-1H-isoindole-1,3(2H)-dione This example illustrates the preparation and analysis of 2-(2,4-difluoro-phenyl)-4,5,6,7-tetrafluoro-1H-isoindole-1,3(2H)-dione ($C_{14}H_3F_6NO_2$) having an exact mass of 331.01 and a molecular weight of about 331.2 (carbon about 50.77%, hydrogen about 0.91%, fluoride about 34.42%, nitrogen about 4.23%, and oxygen about 9.66%).

A mixture of about 1 g (about 7.75 mmol) of 2,4-difluoroaniline, about 1.54 g (about 7 mmol) of tetrafluorophthalic anhydride and about 50 mL of glacial acetic acid was refluxed for about 3.5 hours. The solvent was evaporated to dryness under reduced pressure of from about 200 to about 15 mbar. The residue was dissolved in about 75 mL of $CH_2C_{12}$. The solution was washed three times with about 25 mL of about 0.1 M HCl and twice with about 25 mL of water. The residue was then dried with $Na_2SO_4$. After removal of the solvent, the residue was recrystallized from ethyl alcohol to yield about 980 mg (about 42%) of 2-(2,4-difluorophenyl)-4,5,6,7-tetrafluoro-1H-isoindole-1,3(2H)-dione with a melting point of about 145° to about 146° C.

The $^1$H NMR spectral analysis results were as follows: (DMSO-d6) 7.22-7.38 (m, 1H), 7.50-7.66 (m, 2H). The $^{19}$F NMR spectral analysis results were as follows: (DMSO-d6/CFCl3) −142.3 (m, 2F), −136.9 (m, 2F), −113.8 (m, 1F), −105.6 (m, 1F). The mass spectral (EI) analysis results were as follows: m/z (relative intensity), 331 (M$^+$, 65), 287 (68), 148 (100). Analytically calculated values for the compound $C_{14}H_3NO_2F_6$ were carbon about 50.78%, hydrogen about 0.91%, and nitrogen about 4.23%. As determined from the NMR and mass spectrometry analysis results values for the compound $C_{14}H_3NO_2F_6$ were carbon about 50.60%, hydrogen about 0.83%, and nitrogen about 3.95%.

EXAMPLE 8

HUVEC MTT Assay for Selected Present Invention Thalidomide Analogs

HUVEC MTT assays were performed for the selected thalidomide analogs of the present invention to determine a rough estimate of the efficacy of such compounds in the inhibition of angiogenesis. For the MTT assay, 1.0 to 2.5×10$^3$ cells per well were plated in 96-well plates in 0.1 ml medium, in triplicate. After 24 hours, the cells were exposed to treatment for 5 days. One plate was analyzed every 24 hours by the addition of 20 μL of 5 mg/ml MTT solution (available from Sigma of St. Louis, Mo.) in PBS, to each well for 4 hours. The MTT solution was aspirated and 170 μL DMSO was added to each well to dissolve the formazan crystals. The absorbance at 540 nm was measured using a Biokinetics plate reader (available from Bio-Tek Instruments of Winooski, Vt.). Triplicate wells were assayed for each condition. The assay protocol described herein stems from Kruger et al., a protein kinase C inhibitor, inhibits endothelial cell proliferation and angiogenic hypoxic response, *Invasion and Metastasis*, 18(4): 209-218 (incorporated herein by reference).

The following results for the selected compounds were determined measured utilizing growth curves comparing control wells to treated wells using the MTT assays.

2-(5-hydroxy-2,6-dioxo-piperidin-3-yl)-1H-isoindole-1,3 [2H]-dione (CPS 3)—No cytostatic activity was noted at either 100 μM or at 10 μM.

2-(1-hydroxymethyl-2,6-dioxo-piperidin-3-yl)-1,3-dihydro-2H-isoindole-1,3-dione (CPS11)—Potent inhibition (>90%) at 100 μM was found at about 72 hours. An inhibition of about 60% was found at 10 μM was noted at about 72 hours.

2-(2,4-difluorophenyl)-4,7-dimethyl-1H-isoindole-1,3 (2H)-dione (CPS42)—An inhibition of about 44% was found at 100 μM but no such activity was found at a level of about 10 μM.

1-cyclohexyl-5-ethyl-5-phthalimidobarbituric acid (CPS44)—An inhibition of about 50% was found at 100 μM but no such activity was found at a level of about 10 μM.

5-ethyl-1-phenyl-5-(tetrafluorophthalimido)barbituric acid (CPS45)—Potent inhibition (>90%) at 100 μM and at 10 μM was noted.

5-(tetrafluorophthalimido)pyrimidine-2,4(1H,3H)-dione (CPS48) Potent inhibition (about 85%) at 100 μM and at 10 μM was noted.

2-(2,4-difluoro-phenyl)-4,5,6,7-tetrafluoro-1H-isoindole-1,3(2H)-dione (CPS49)—A potent inhibition of about 90% was found at 100 μM but no such activity was found at a level of about 10 μM.

EXAMPLE 9

Figure 2:
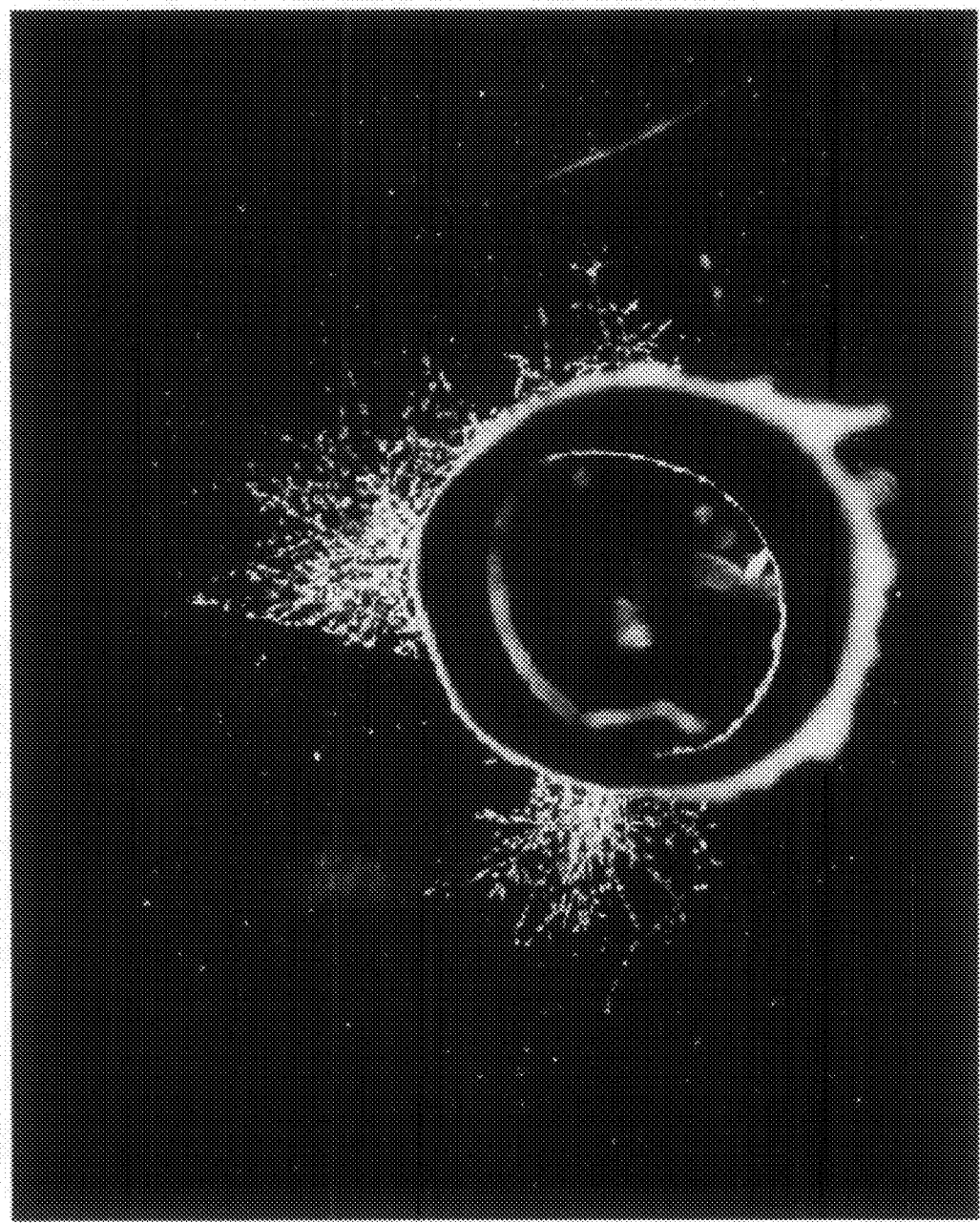
FIG. 2 is a photomicrograph of a rat aorta ring treated with CPS3.

Anti-angiogenic Activity Analysis Results for Selected Present Invention Thalidomide Analogs Measured Utilizing Rat Aortic Rings The efficacy of selected thalidomide analogs of the present invention was studied by five-day treatment of rat aortic rings (utilizing Sprague-Dawley rats available from Charles River Labs) with varied doses of the analogs. A DMSO control was utilized (FIG. 1). The results, determined using image analysis comparing control rings versus the treated rings (using NIM Image software), of the studies are as follows:

2-(5-hydroxy-2,6-dioxo-piperidin-3-yl)-1H-isoindole-1,3 [2H]-dione (CPS3)—A daily dosage of 100 µM showed about a 50% angiogenesis inhibition activity (FIG. 2).

Figure 3:
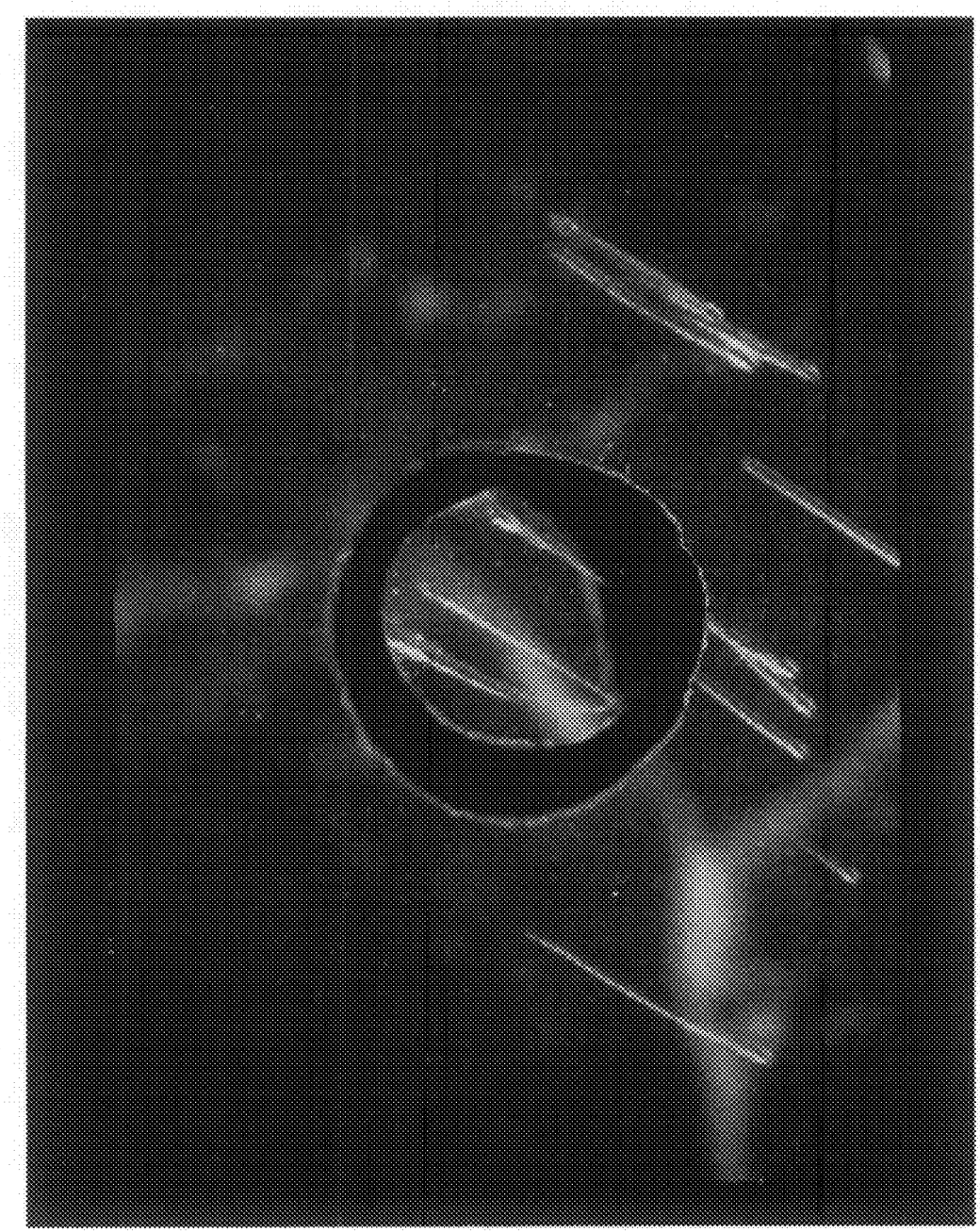
FIG. 3 is a photomicrograph of a rat aorta ring treated with about 100 µM of CPS11.
Figure 4:
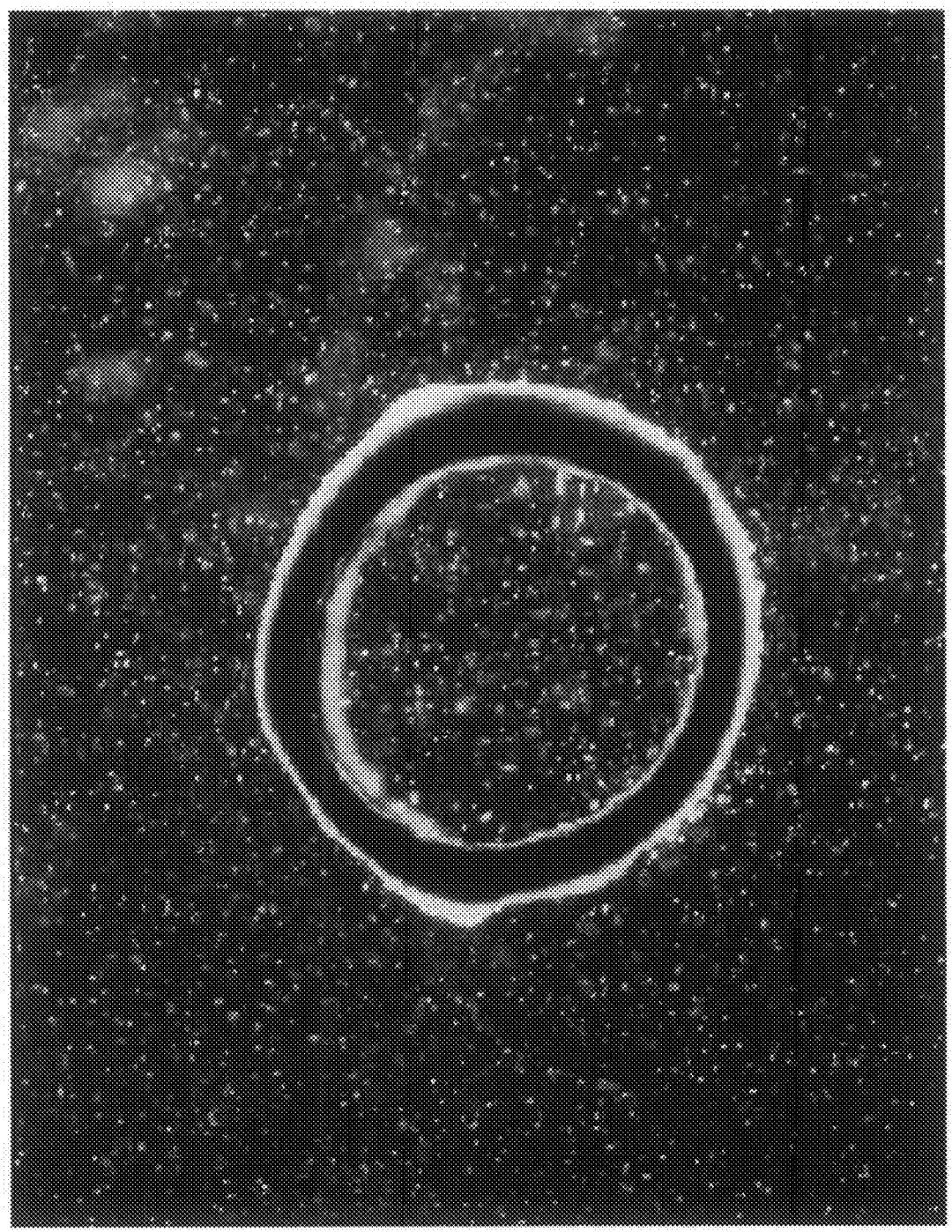
FIG. 4 is a photomicrograph of another rat aorta ring treated with about 100 µM of CPS11.
Figure 5:
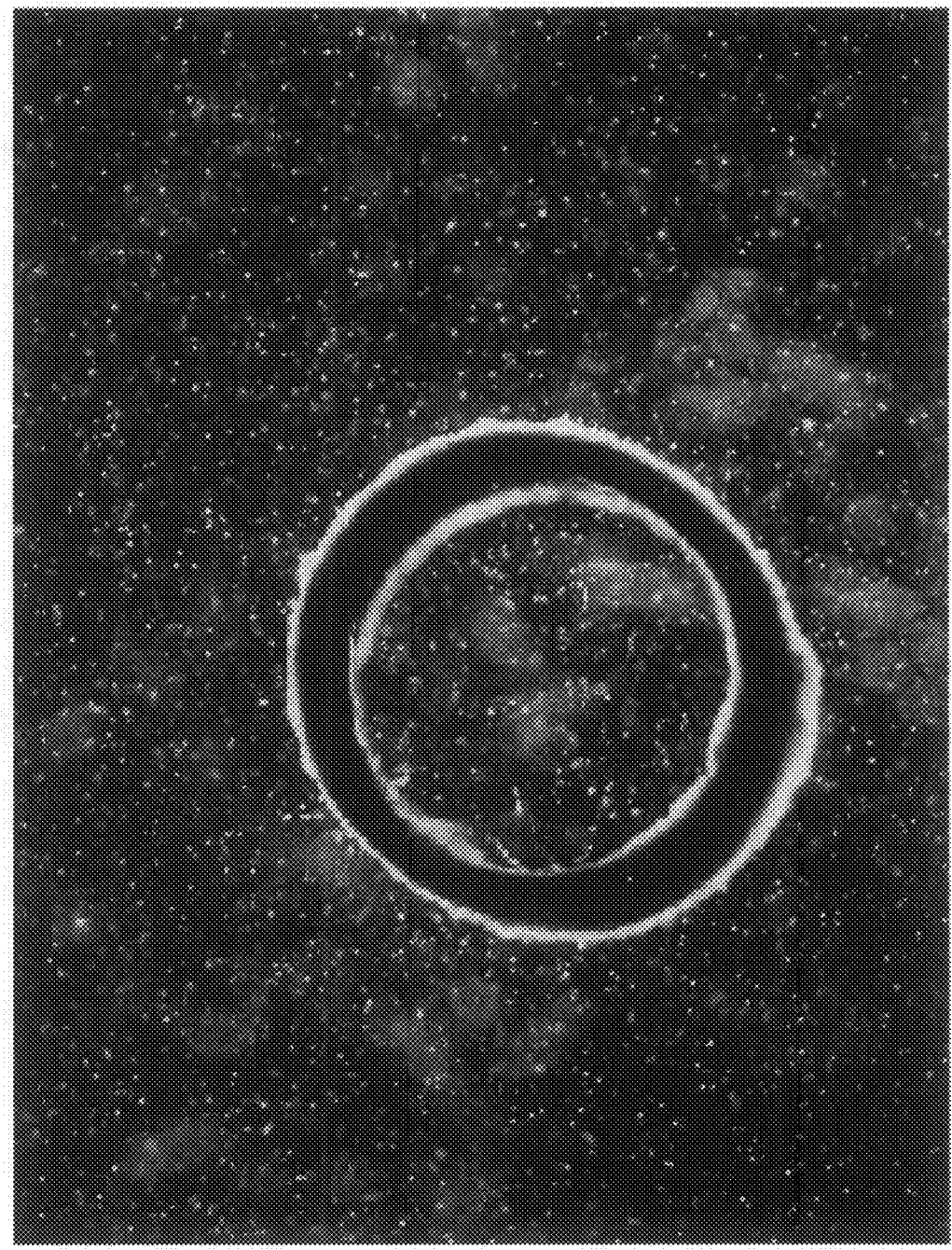
FIG. 5 is a photomicrograph of another rat aorta ring treated with about 100 µM of CPS11.

2-(1-hydroxymethyl-2,6-dioxo-piperidin-3-yl)-1,3-dihydro-2H-isoindole-1,3-dione (CPS11)—A daily dosage of 100 µM showed a potent 90% angiogenesis inhibition activity (FIGS. 3-5).

Figure 6:
FIG. 6 is a photomicrograph of a rat aorta ring treated with about 100 µM of CPS44.

1-cyclohexyl-5-ethyl-5-phthalimidobarbituric acid (CPS44)—No inhibition of angiogenesis was found at 100 µM (FIG. 6).

Figure 7:
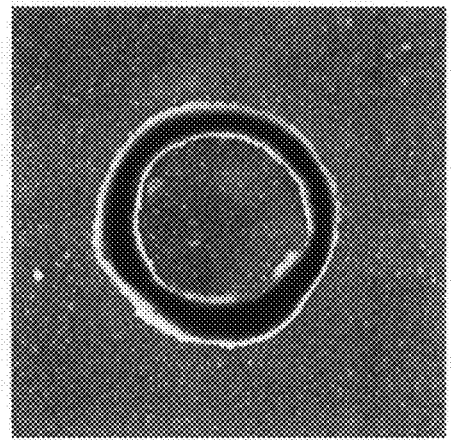
FIG. 7 is a photomicrograph of a rat aorta ring treated with about 100 µM of CPS45.

5-ethyl-1-phenyl-5-(tetrafluorophthalimido)barbituric acid (CPS45)—A daily dosage of 100 µM showed a potent 90% angiogenesis inhibition activity (FIG. 7).

Figure 8:
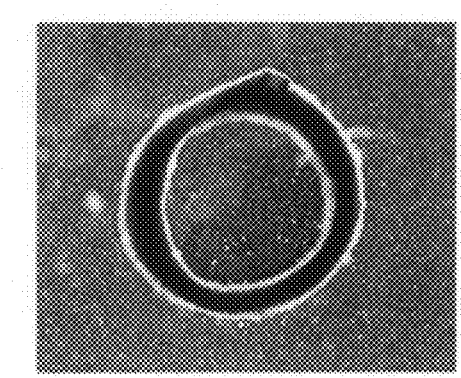
FIG. 8 is a photomicrograph of another rat aorta ring treated with about 100 µM of CPS48.

5-(tetrafluorophthalimido)pyrimidine-2,4(1H,3H)-dione (CPS48)—A daily dosage of 100 µM showed a potent 90% angiogenesis inhibition activity (FIG. 8).

Figure 9:
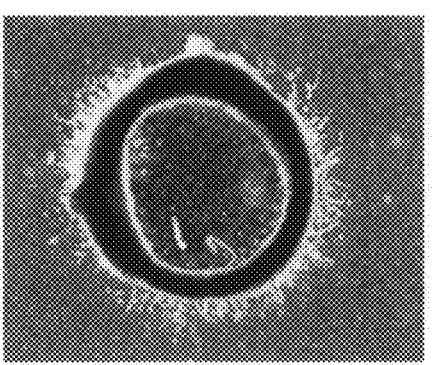
FIG. 9 is a photomicrograph of another rat aorta ring treated with about 100 µM of CPS49.

2-(2,4-difluoro-phenyl)-4,5,6,7-tetrafluoro-1H-isoindole-1,3(2H)-dione (CPS49)—A daily dosage of 100 µM showed extensive angiogenesis inhibition activity (FIG. 9).

EXAMPLE 10

Anti-angiogenic Activity Analysis Results for 2-(1-hydroxymethyl-2,6-dioxo-piperidin-3-yl)-1,3-dihydro-2H-isoindole-1,3-dione (CPS11) Measured Utilizing Human Saphenous Vein The efficacy of 2-(1-hydroxymethyl-2,6-dioxo-piperidin-3-yl)-1,3-dihydro-2H-isoindole-1,3-dione (CPS11) was studied by 14 day treatment of human saphenous veins (obtained through an IRB-approved protocol, Surgery Brand NCI) with 100 µM doses of the analog. A CAI, carboxyamido-triazole, 12 µg/ml control was utilized. The results of such studies using image analysis as discussed above, indicate that daily dosages of 100 µM of 2-(1-hydroxymethyl-2,6-dioxo-piperidin-3-yl)-1,3-dihydro-2H-isoindole-1,3-dione (CPS11) showed a potent 90% angiogenesis inhibition activity level.

EXAMPLE 11

Toxicology Screen Analysis Results for Selected Present Invention Thalidomide Analogs Toxicology screen studies have been performed for the thalidomide analogs of the present invention. The results of such toxicology screening studies for selected thalidomide analogs are as follows:

2-(1-hydroxymethyl-2,6-dioxo-piperidin-3-yl)-1,3-dihydro-2H-isoindole-1,3-dione (CPS11)—Treatment was safe at dosage levels of 10 and 100 mg/kg, i.p., single dose. Some amount of sedation was noted.

2-(2,4-difluorophenyl)-4,7-dimethyl-1H-isoindole-1,3 (2H)-dione (CPS42)—Treatment was safe at a dosage level 200 mg/kg, i.p., single dose. Slight sedation was noted within 15 minutes of injection.

5-ethyl-1-phenyl-5-(tetrafluorophthalimido)barbituric acid (CPS45) —A dose of 200 mg/kg, i.p., single dose, was a lethal dose. Animals treated with such dosage died within 2.5 hours of treatment.

2-(2,4-difluoro-phenyl)-4,5,6,7-tetrafluoro-1H-isoindole-1,3(2H)-dione (CPS49)—A dose of 200 mg/kg, i.p., single dose, was a lethal dose. Animals treated with such dosage died within 18 hours of treatment.

EXAMPLE 12

Methods of Treatment

The present invention includes a treatment for undesirable angiogenesis and angiogenesis dependent or associated diseases, in a subject such as an animal, for example a rat or human. The method includes administering one or more of the compounds of the present invention, or a combination of one or more of the compounds and one or more other pharmaceutical agents, to the subject in a pharmaceutically compatible carrier. The administration is made in an amount effective to inhibit the development or progression of angiogenesis and diseases associated with the same. Although the treatment can be used prophylactically in any patient in a demographic group at significant risk for such diseases, subjects can also be selected using more specific criteria, such as a definitive diagnosis of the condition.

The vehicle in which the drug is delivered can include pharmaceutically acceptable compositions of the drugs, using methods well known to those with skill in the art. Any of the common carriers, such as sterile saline or glucose solution, can be utilized with the drugs provided by the invention. Routes of administration include but are not limited to oral and parenteral routes, such as intravenous (iv), intraperitoneal (ip), rectal, topical, ophthalmic, nasal, and transdermal.

The drugs may be administered in a suitable manner now known or later developed, e.g., orally or intravenously, in any conventional medium. For example, intravenous injection may be by an aqueous saline medium. The medium may also contain conventional pharmaceutical adjunct materials such as, for example, pharmaceutically acceptable salts to adjust the osmotic pressure, lipid carriers such as cyclodextrins, proteins such as serum albumin, hydrophilic agents such as methyl cellulose, detergents, buffers, preservatives and the like. A more complete explanation of parenteral pharmaceutical carriers can be found in *Remington: The Science and Practice of Pharmacy* (19$^{th}$ Edition, 1995) in chapter 95.

Embodiments of other pharmaceutical compositions can be prepared with conventional pharmaceutically acceptable carriers, adjuvants and counterions as would be known to those of skill in the art. The compositions are preferably in the form of a unit dose in solid, semi-solid and liquid dosage forms such as tablets, pills, powders, liquid solutions or suspensions.

The compounds of the present invention are ideally administered as soon as possible after detected unwanted angiogenesis. For example, once unwanted angiogenesis has been confirmed or the presence of a tumor has been identified, a therapeutically effective amount of the drug is administered. The dose can be given orally or by frequent bolus administration.

Therapeutically effective doses of the compounds of the present invention can be determined by one of skill in the art, with a goal of achieving a desired level of anti-angiogenesis as illustrated in the foregoing examples. The relative toxicities of the compounds make it possible to administer in various dosage ranges. An example of such a dosage range is from about 0.5 to about 50 mg/kg body weight orally in single or divided doses. Another example of a dosage range is from about 0.5 to about 50 mg/kg body weight orally in single or divided doses. For oral administration, the compositions are, for example, provided in the form of a tablet containing from about 25 to about 500 mg of the active ingredient, particularly 100 mg of the active ingredient for the symptomatic adjustment of the dosage to the subject being treated.

The specific dose level and frequency of dosage for any particular subject may be varied and will depend upon a variety of factors, including the activity of the specific compound, the extent of existing angiogenic activity, the age, body weight, general health, sex, diet, mode and time of administration, rate of excretion, drug combination, and severity of the condition of the host undergoing therapy.

The pharmaceutical compositions can be used in the treatment of a variety of diseases mediated by angiogenesis. Examples of such diseases include all types of cancer, ocular neovascular disease, solid tumor formation and metastasis in solid tumors such as rhabdomyosarcomas, retinoblastoma, Ewing sarcoma, neuroblastoma, osteosarcoma, colon, prostate, head and neck, breast, bladder, liver, pancreatic, lung, CNS, and blood-born tumors such as leukemia, also diseases such as hemangioma, ulcerative colitis, Crohn's disease, diabetic retinopathy, macular degeneration, sickle cell anemia, sarcoid, syphilis, pseudoxanthoma elasticum, Paget's disease, vein occlusion, artery occlusion, carotid obstructive disease, chronic uveitis/vitritis, mycobacterial infections, Lyme's disease, systemic lupus erythematosis, retinopathy of prematurity, Eale's disease, Bechet's disease, infections causing a retinitis or choroiditis, presumed ocular histoplasmosis, Best's disease, myopia, optic pits, Stargart's disease, pars planitis, chronic retinal detachment, hyperviscosity syndromes, toxoplasmosis, trauma and post-laser complications. Other diseases include, but are not limited to, diseases associated with rubeosis (neovasculariation of the angle) and diseases caused by the abnormal proliferation of fibrovascular or fibrous tissue including all forms of proliferative vitreoretinopathy.

EXAMPLE 13

Combination Therapy

The present invention also includes combinations of the thalidomide analogs of the present invention and/or combination of the same with various other angiogenesis inhibitor compounds. For example, the compounds of this invention may be administered in combination with effective doses of other anti-angiogenic agents. The term "administration" refers to both concurrent and sequential administration of the active agents. Examples of anti-angiogenic agents that can be used in combination with the thalidomide analogs of the present invention are TNP-470, carbonic anhydrase inhibitors, endostatin, angiostatin, 2-methoxyestradiol, IMiD (Immune-modulating inhibitor drug) CC5013, matrix metalloproteinase inhibitors, and COL-3. In addition, the thalidomide analogs of this invention may be used in combination with other forms of cancer therapy, e.g., chemotherapy, radiation therapy, hormonal therapy).

In view of the many possible embodiments to which the principles of our invention may be applied, it should be recognized that the illustrated embodiment is only a preferred example of the invention and should not be taken as a limitation on the scope of the invention. Rather, the scope of the invention is defined by the following claims. We therefore claim as our invention all that comes within the scope and spirit of these claims.

We claim:

1. A composition that inhibits angiogenesis in a subject when administered in an effective amount, wherein the composition comprises one or more compounds having the following formula or pharmaceutically acceptable salts thereof;

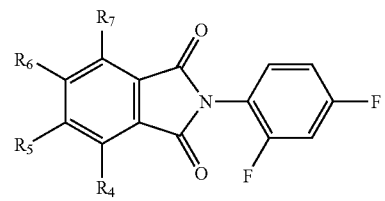

wherein R4 through R7 are, independently, a halogen, or R5 and R6 are hydrogen and R4 and R7 are methyl groups.

2. The composition of claim 1, wherein the compound is:

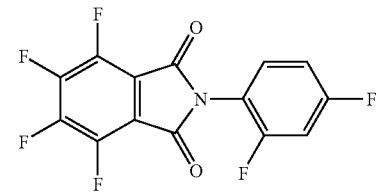 [SMILES: O=C1c2c(F)c(F)c(F)c(F)c2C(=O)N1c1ccc(F)cc1F]

or a pharmaceutically acceptable salt thereof.

3. The composition of claim 1, wherein the compound is:

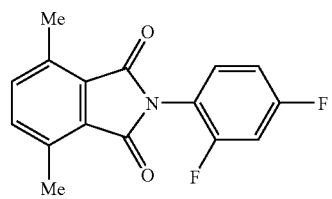 [SMILES: Cc1ccc(C)c2c1C(=O)N(c1ccc(F)cc1F)C2=O]

or a pharmaceutically acceptable salt thereof.

4. The composition of claim 1, further comprising a pharmaceutically acceptable carrier.

5. The composition of claim 2, further comprising a pharmaceutically acceptable carrier.

6. The composition of claim 3, further comprising a pharmaceutically acceptable carrier.

* * * * *